(12) United States Patent
Christadoss et al.

(10) Patent No.: US 7,923,010 B2
(45) Date of Patent: Apr. 12, 2011

(54) METHODS AND MATERIALS FOR TREATING AUTOIMMUNE DISEASES AND CONDITIONS

(75) Inventors: Premkumar Christadoss, League City, TX (US); Erdem Tuzun, Philadelphia, PA (US)

(73) Assignee: The Board of Regents of the University of Texas System, Austin, TX (US)

( * ) Notice: Subject to any disclaimer, the term of this patent is extended or adjusted under 35 U.S.C. 154(b) by 1057 days.

(21) Appl. No.: 10/571,379

(22) PCT Filed: Sep. 11, 2004

(86) PCT No.: PCT/US2004/029673
§ 371 (c)(1),
(2), (4) Date: Mar. 20, 2007

(87) PCT Pub. No.: WO2005/025509
PCT Pub. Date: Mar. 24, 2005

(65) Prior Publication Data
US 2007/0243187 A1 Oct. 18, 2007

Related U.S. Application Data

(60) Provisional application No. 60/502,086, filed on Sep. 11, 2003.

(51) Int. Cl.
*A61K 39/00* (2006.01)
*A61K 39/395* (2006.01)

(52) U.S. Cl. ............... 424/133.1; 424/141.1; 424/145.1
(58) Field of Classification Search ...................... None
See application file for complete search history.

(56) References Cited

U.S. PATENT DOCUMENTS

| 5,977,076 | A | * | 11/1999 | Anderson et al. | ............... 514/19 |
| 6,180,370 | B1 | * | 1/2001 | Queen et al. | ................. 435/69.6 |
| 6,492,403 | B1 | * | 12/2002 | Illig et al. | ..................... 514/365 |
| 7,511,121 | B2 | * | 3/2009 | Arnason et al. | ............. 530/387.1 |
| 2005/0019326 | A1 | * | 1/2005 | Stahl | .......................... 424/145.1 |

FOREIGN PATENT DOCUMENTS

WO  WO 85/02261  *  5/1985

OTHER PUBLICATIONS

Wang, Y et al. Proc. Nat. Acad. Sci. USA [1996] 93:8563-8568.*
Van Noort et al, International Reivew of Cytology 178: 127-205, 1998.*
Witte et al, Cancer and Metastasis Reviews 17: 155-161, 1998.*

* cited by examiner

*Primary Examiner* — Phuong Huynh
(74) *Attorney, Agent, or Firm* — Benjamin Aaron Adler

(57) ABSTRACT

Disclosed are methods for treating an autoimmune disease or condition in a subject. The methods include administering to the subject a compound which inhibits the subject's classical complement pathway. Also disclosed are methods for suppressing hyperacute graft rejection in a subject. The methods include administering to the subject a compound which inhibits the subject's classical complement pathway. Compositions which include a specific inhibitor of C1q and a pharmaceutically acceptable excipient are also described.

1 Claim, 9 Drawing Sheets

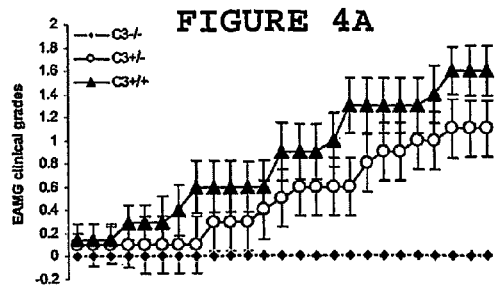
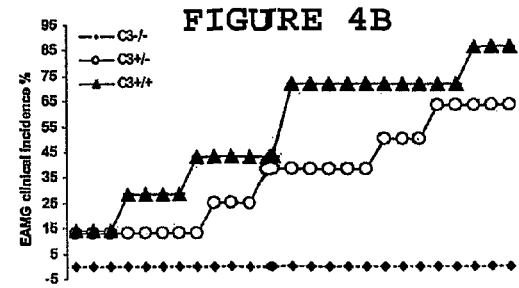
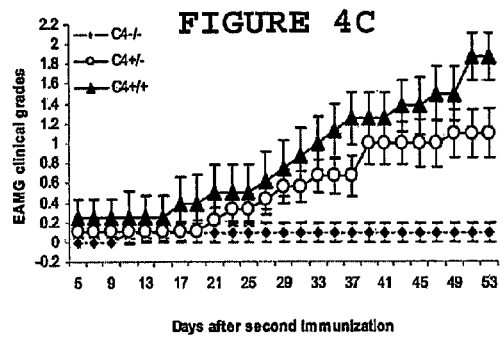
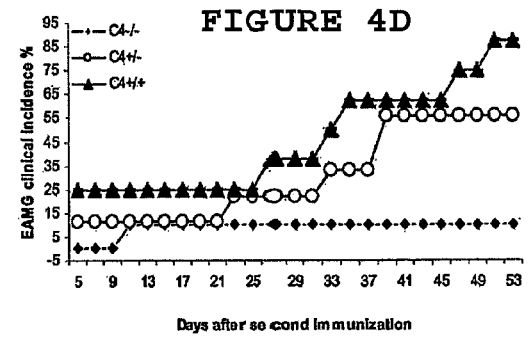
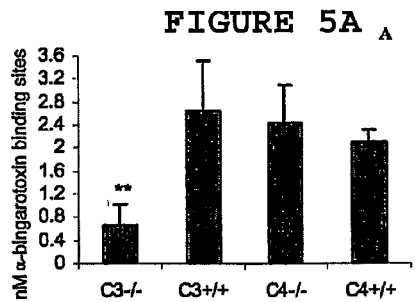
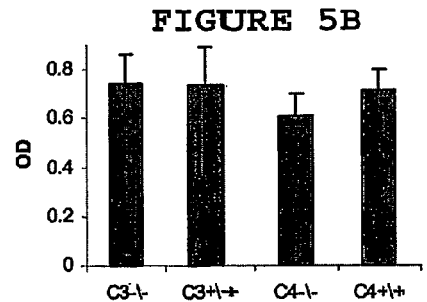
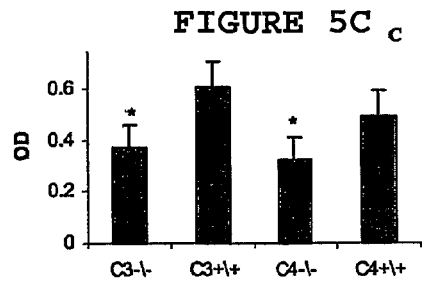
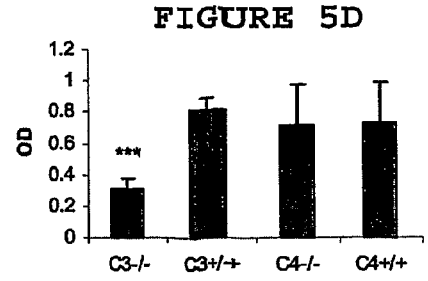

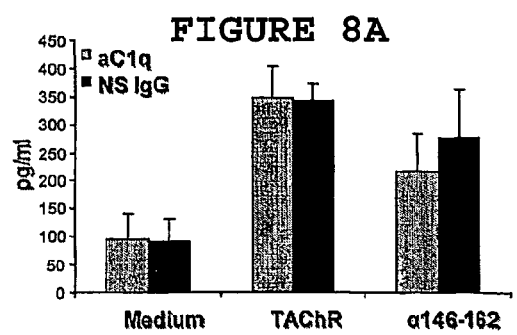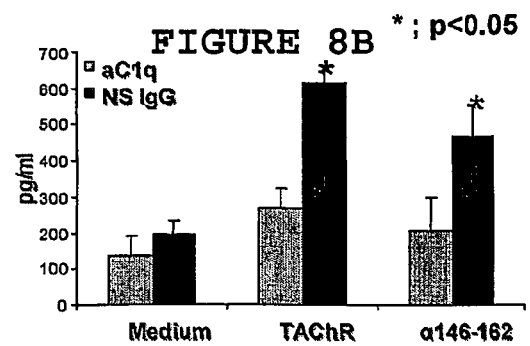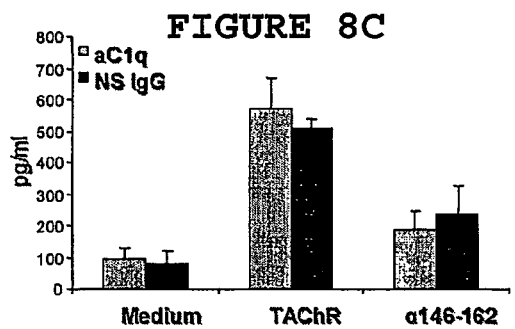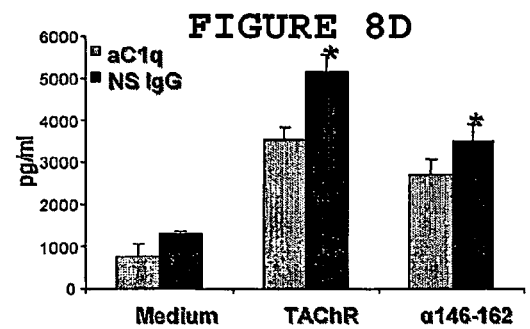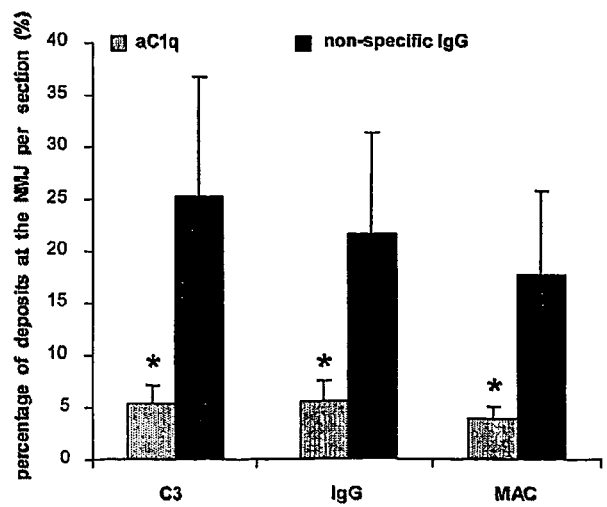

PNA-binding spleen cells

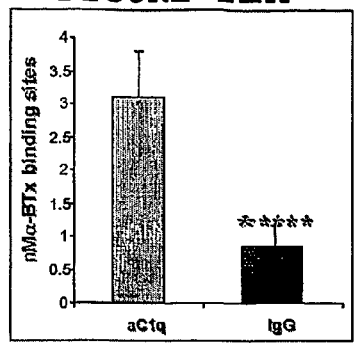
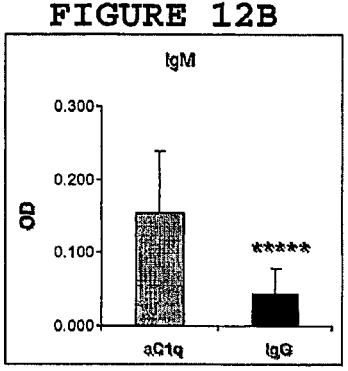
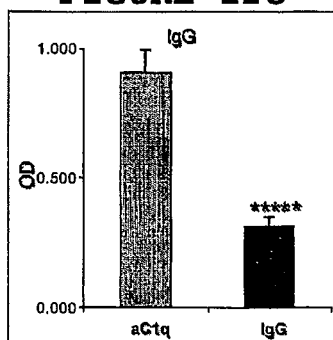
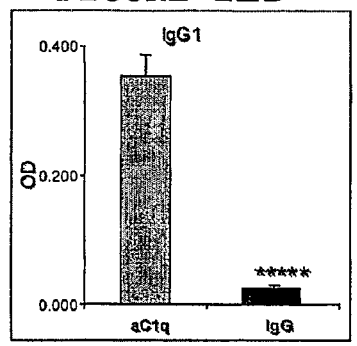
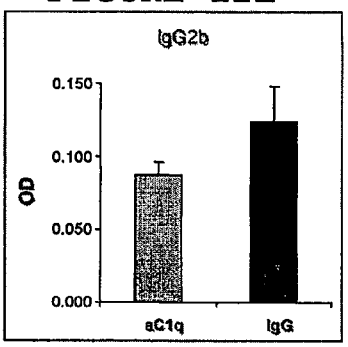
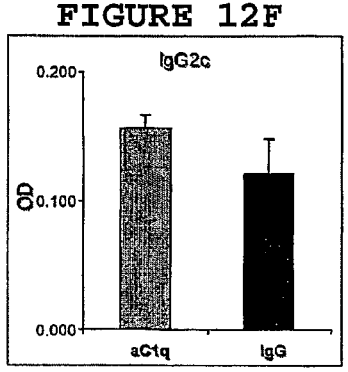
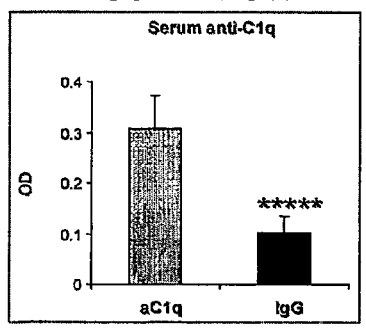
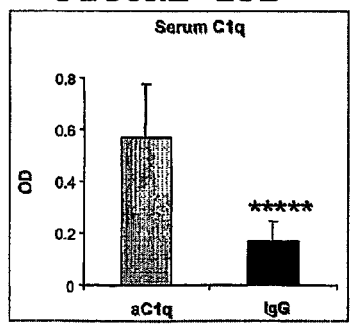
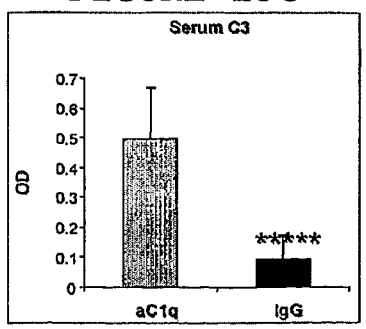
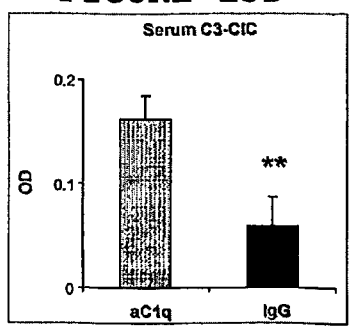

METHODS AND MATERIALS FOR TREATING AUTOIMMUNE DISEASES AND CONDITIONS

The present invention claims the benefit of U.S. Provisional Patent Application Ser. No. 60/502,086, filed Sep. 11, 2003, which is hereby incorporated by reference.

FIELD OF THE INVENTION

The present invention is directed to methods and materials for treating autoimmune diseases and, more particularly, to methods and materials for treating myasthenia gravis.

BACKGROUND OF THE INVENTION

Autoimmune diseases afflict large numbers of individuals in the U.S. and worldwide.

For example, Myasthenia gravis ("MG"), an autoimmune neuromuscular disease, afflicts about 30,000 individuals in the United States and about 625,000 individuals worldwide. Neuromuscular transmission fails in MG because of decreased sensitivity of the postsynaptic membrane to the neurotransmitter acetylcholine ("ACh"), which results from a loss of acetylcholine receptors ("AChRs") due to a T-cell and B-cell mediated autoimmune attack against the AChR (Christadoss et al., "Immunotherapy for Myasthenia Gravis: a Murine Model," *J. Immunol.*, 136(7):2437-2440 (1986)). Pemphigus, a group of autoimmune blistering diseases of the skin and/or mucous membranes, afflicts about 12,000 individuals in the United States and about 250,000 individuals worldwide. Autoimmune hemolytic anemia, a condition in which the immune system attacks the red blood cells, resulting in fewer of these oxygen-transporting cells, afflicts about 12,000 individuals in the United States and about 280,000 individuals worldwide. Idiopathic thrombocytopenic purpura, a bleeding disorder characterized by the destruction of platelets by the immune system, resulting in too few platelets in the blood, afflicts about 12,000 individuals in the United States and about 250,000 individuals worldwide. Autoimmune glomerulonephritis, a nephritis which is accompanied by inflammation of the capillary loops in the glomeruli of the kidney, afflicts about 60,000 individuals in the United States and over a million individuals worldwide.

Still other examples of autoimmune diseases that afflict large numbers of individuals in the U.S. and worldwide include Type I diabetes, rheumatoid arthritis, Hashimoto's disease, Graves disease, dermatomyositis, autoimmune vitiligo, psoriasis, and Guillain-Barre syndrome.

At present, many autoimmune diseases are treated using non-specific immunosuppressive drugs, such as steroids. However, steroids can have long-term side-effects, and they can suppress desirable immune responses. Non-steroidal immunosuppressive drugs have also been developed. For example, Eculizumab is a humanized monoclonal antibody that prevents the cleavage of human complement component C5 into pro-inflammatory components, and it has been approved to treat rheumatoid arthritis, nephritis, and phemphigus. However, use of this monoclonal antibody must be carefully monitored, as it can reduce a patient's ability to clear viruses, bacteria, and apoptotic and tumor cells, thus making patients more susceptible to bacterial and viral infection.

In view of the above, a need remains for methods and materials for treating autoimmune diseases. The present invention is directed, in part, to addressing this need.

SUMMARY OF THE INVENTION

The present invention relates to a method for treating an autoimmune disease or condition in a subject. The method includes administering to the subject a compound which inhibits the subject's classical complement pathway.

The present invention also relates to a method for suppressing hyperacute graft rejection in a subject. The method includes administering to the subject a compound which inhibits the subject's classical complement pathway.

The present invention also relates to a composition which includes a specific inhibitor of C1q and a pharmaceutically acceptable excipient.

BRIEF DESCRIPTION OF THE DRAWINGS

FIGS. 4A and 4B are graphs showing the effect of C3 gene deletion on clinical EAMG development in terms of EAMG severity (FIG. 4A) and EAMG incidence (FIG. 4B). FIGS. 4C and 4D are graphs showing the effect of C4 gene deletion on clinical EAMG development in terms of EAMG severity (FIG. 4C) and EAMG incidence (FIG. 4D).

FIGS. 5A-5D are bar graphs showing serum anti-AChR levels in C3 and C4 knockout mice. FIG. 5A shows the anti-AChR IgG levels (determined by RIA); FIG. 5B shows the anti-AChR IgG1 levels (determined by ELISA); FIG. 5C shows the anti-AChR IgG2b levels (determined by ELISA); and FIG. 5D shows the total IgG levels (determined by ELISA).

FIG. 8A-8D are bar graphs showing cytokine production profiles (IL-2 (FIG. 8A); IL-6 (FIG. 8B); IL-10 (FIG. 8C); and IFN-γ (FIG. 8D)) of anti-C1q-treated mice and control IgG-treated mice.

FIG. 9 is a bar graph showing the effect of anti-C1q treatment on NMJ complement and IgG deposition.

FIGS. 12A-12F are bar graphs showing serum anti-AChR levels in anti-C1q-treated mice and control IgG-treated mice.

FIGS. 13A-13D are bar graphs showing serum C1q-CIC levels (FIG. 13A), serum C1q levels (FIG. 13B), serum C3 levels (FIG. 13C), and serum C3-CIC levels (FIG. 13B) in anti-C1q-treated mice and control IgG-treated mice.

DETAILED DESCRIPTION OF THE INVENTION

Figure 1:
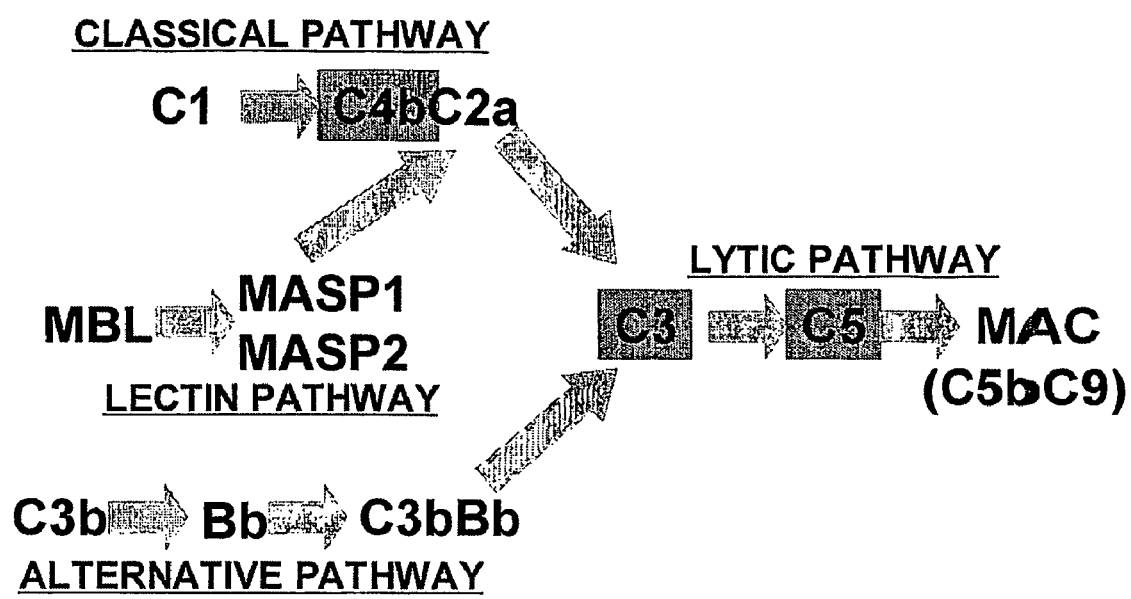
FIG. 1 is a graphic illustrating three separate complement pathways (classical, mannose binding lectin ("MBL"), and alternative pathways) and the complement components of each of the pathways.

One aspect of the present invention relates to a method for treating an autoimmune disease or condition in a subject. The method includes administering to the subject a compound which inhibits the subject's classical complement pathway.

Another aspect of the present invention relates to a method for suppressing hyperacute graft rejection in a subject. The method includes administering to the subject a compound which inhibits the subject's classical complement pathway.

As used herein, "autoimmune disease or condition" is meant to refer to a disease or condition which results from or is exacerbated by the body's immune system attack on its own cells, tissues, organs, and/or systems, for example those of the blood, the digestive tract, the eyes, the glands, the heart, the joints, the kidneys, the lungs, the muscles, the nerves, the brain, the connective tissue, and the skin. Examples of such autoimmune diseases or conditions include those in which the complement plays a role in disease pathogenesis, such as Type I diabetes, rheumatoid arthritis, Hashimoto's disease, Graves disease, dermatomyositis, autoimmune vitiligo, psoriasis, Guillain-Barre syndrome, and Kawasaki syndrome. Other examples include antibody dependent complement mediated autoimmune diseases, such as myasthenia gravis, pemphigus, autoimmune hemolytic anemia, idiopathic thrombocytopenic purpura, autoimmune glomerulonephritis (e.g., autoimmune forms of membranoproliferative glomerulonephritis), and anti-glomerular basement membrane nephritis.

"Treatment" as used herein, is meant to refer to both therapeutic treatments (for example, as in the case where the subject already shows one or more clinical signs of the autoimmune disease or condition), as well as to preventative treatments (for example, as in the case where the subject does not show any clinical signs of the autoimmune disease or condition and during remissions of the disease or condition). In the former case, therapeutic treatment can be carried out to stop or impede progression of the disease or condition, or to reverse its progression, or to stop, impede, or reverse one or more symptoms or other manifestations of the disease or condition. In the latter case, preventative treatment can be carried out to reduce the risk that the subject will develop the disease or condition or one or more symptoms or other manifestations of the disease or condition or to prevent or otherwise reduce the risk of relapse of the disease or condition.

"Suppressing", as used herein in the context of hyperacute graft rejection, is meant to refer to any quantitatively or qualitatively measurable or observable reduction in hyperacute graft rejection of, for example, a tissue graft of an organ, such as of a kidney, a liver, a lung, a heart, and/or an eye.

"Subject", as used herein, is meant to include mammals, such as mice, rats, cats, dogs, monkeys, bovine, porcine, equine, and humans. Suitable human subjects include, for example, those who have previously been diagnosed as being afflicted with a particular autoimmune disease or condition (such as any one or more of those described above); those who have previously been determined to be at risk of developing a particular autoimmune disease or condition (such as any one or more of those described above); those who have not previously been diagnosed as being afflicted with a particular autoimmune disease or condition (such as any one or more of those described above); and/or those who have not previously been determined to be at risk of developing a particular autoimmune disease or condition (such as any one or more of those described above). Other suitable human subjects include, for example, those who have recently undergone a grafting procedure, as well as those who are about to undergo a grafting procedure.

As discussed above, the method includes administering to the subject a compound which inhibits the subject's classical complement pathway. The inhibition can be direct or indirect, and it can be selective or non-selective. As used herein, classical complement pathway inhibition is to be deemed to be "selective" when at least one other pathway to complement activation (e.g., the MBL pathway and/or the alternative pathway) is not substantially inhibited (e.g., inhibited by less than about 50%, such as by less than about 40%, by less than about 30%, by less than about 20%, by less than about 10%, etc.). Inhibition of the classical complement pathway can be specific, as in the case where both the MBL pathway and the alternative pathway are not substantially inhibited (e.g., inhibited by less than about 50%, such as by less than about 40%, by less than about 30%, by less than about 20%, by less than about 10%, etc.).

Inhibition of the classical complement pathway can be carried out, for example, by using a compound that inhibits C1q, C2, and/or C4 complement proteins. In one embodiment, the compound inhibits the subject's classical complement pathway by selectively inhibiting C1q. As used herein, a compound is to be deemed to "selectively" inhibit C1q when at least one of the other components in the classical complement pathway (e.g., C2 and/or C4) is not substantially inhibited by the compound (e.g., inhibited by less than about 50%, such as by less than about 40%, by less than about 30%, by less than about 20%, by less than about 10%, etc.). In another embodiment, the compound inhibits the subject's classical complement pathway by selectively inhibiting C2. As used herein, a compound is to be deemed to "selectively" inhibit C2 when at least one of the other components in the classical complement pathway (e.g., C1q and/or C4) is not substantially inhibited by the compound (e.g., inhibited by less than about 50%, such as by less than about 40%, by less than about 30%, by less than about 20%, by less than about 10%, etc.). In yet another embodiment, the compound inhibits the subject's classical complement pathway by selectively inhibiting C4. As used herein, a compound is to be deemed to "selectively" inhibit C4 when at least one of the other components in the classical complement pathway (e.g., C1q and/or C2) is not substantially inhibited by the compound (e.g., inhibited by less than about 50%, such as by less than about 40%, by less than about 30%, by less than about 20%, by less than about 10%, etc.).

The compound can be a specific inhibitor of C1q. In this regard, a compound is to be deemed to be a "specific" inhibitor of C1q when the compound inhibits C1q; does not substantially inhibit C2 and/or C4; and does not substantially inhibit the MBL pathway and/or the alternative pathway. Alternatively, the compound can be a specific inhibitor of C2. In this regard, a compound is to be deemed to be a "specific"

inhibitor of C2 when the compound inhibits C2; does not substantially inhibit C1q and/or C4; and does not substantially inhibit the MBL pathway and/or the alternative pathway. Still alternatively, the compound can be a specific inhibitor of C4. In this regard, a compound is to be deemed to be a "specific" inhibitor of C4 when the compound inhibits C4; does not substantially inhibit C1q and/or C2; and does not substantially inhibit the MBL pathway and/or the alternative pathway.

Examples of compounds that can be used in the practice of the methods of the present invention include anti-C1q antibodies, anti-C2 antibodies, and anti-C4 antibodies. These antibodies can be monoclonal or polyclonal, and, depending on the subject to whom they are to be administered, they can be chimeric. For example, where the subject is a human, chimeric humanized anti-C1q antibodies can be employed; chimeric humanized anti-C2 antibodies can be employed; or chimeric humanized anti-C4 antibodies can be employed.

The aforementioned anti-C1q antibodies, anti-C2 antibodies, and anti-C4 antibodies can be prepared by conventional methods.

Monoclonal antibodies that bind to C1q, C2, or C4 can be produced by hybridomas. A hybridoma is an immortalized cell line which is capable of secreting a specific monoclonal antibody.

In general, techniques for preparing polyclonal and monoclonal antibodies as well as hybridomas capable of producing the desired antibodies are well known in the art. See, e.g., Campbell, *Monoclonal Antibody Technology: Laboratory Techniques in Biochemistry and Molecular Biology*, Amsterdam, The Netherlands: Elsevier Science Publishers (1984) ("Campbell"); and St. Groth et al., *J. Immunol. Methods.*, 35:1-21 (1980), which are hereby incorporated by reference. Any animal (mouse, rabbit, etc.) which is known to produce antibodies can be immunized with the antigenic material C1q, C2, C4, combinations thereof, or an antigenic fragment thereof. Methods for immunization are well known in the art. Such methods include subcutaneous or intraperitoneal injection of the antigenic material. One skilled in the art will recognize that the amount of antigenic material used for immunization will vary based on the animal which is immunized, the antigenicity of the antigenic material, and the site of injection.

The antigenic material (C1q, C2, C4, combinations thereof, or an antigenic fragment thereof) which is used as an immunogen may be modified or administered in an adjuvant in order to increase the antigenic materials antigenicity. Methods of increasing the antigenicity of an antigenic material are well known in the art and include, but are not limited to, coupling the antigen with a heterologous protein (such as a globulin or beta-galactosidase) or including an adjuvant during immunization.

For monoclonal antibodies, spleen cells from the immunized animals are removed, fused with myeloma cells, such as SP2/O-Ag 15 myeloma cells, and allowed to become monoclonal-antibody-producing hybridoma cells.

Any one of a number of methods well known in the art can be used to identify the hybridoma cell which produces an antibody with the desired characteristics. These include screening the hybridomas using, for example, an ELISA assay, a western blot analysis, or a radioimmunoassay. See, e.g., Lutz et al., *Exp. Cell Res.*, 175:109-124 (1988), which is hereby incorporated by reference.

Hybridomas secreting the desired antibodies are cloned, and the class and subclass are determined using procedures known in the art, such as those set described in Campbell, which is hereby incorporated by reference.

For polyclonal antibodies, antibody containing antisera is isolated from the immunized animal and is screened for the presence of antibodies with the desired specificity using one of the above-described procedures.

"Antibodies", as used herein are meant to include antibody fragments, such as Fab, Fab2, and Fc fragments, as well as humanized forms. Humanized forms of the antibodies can be generated using one of the procedures known in the art, such as chimerization. Such methods are described, for example, in U.S. Pat. No. 4,816,567 to Cabilly et al.; Mage et al., pp. 79-97 in *Monoclonal Antibody Production Techniques and Applications*, New York: Marcel Dekker, Inc. (1987); Jones et al., *Nature*, 321:522-525 (1986); Reichmann et al., *Nature*, 332:323-329 (1988); and Presta, *Curr. Op. Struct. Biol.*, 2:593-596 (1992); Perisic et al., *Structure*, 2:1217-1226 (1994); Pei et al., *PNAS*, 94:9637-9642 (1997); Hollinger et al., *Protein Engineering*, 9:299-305 (1996); and Millstein et al., *Nature*, 305:537-539 (1983); which are hereby incorporated by reference.

Antigenic C1q can be prepared, for example, using the methods described in Yonemasu et al., "Purification and Characterization of Subcomponent C1q of the First Component of Bovine Complement," *J. Biochem.*, 88:1545-1554 (1980), which is hereby incorporated by reference. Antigenic C4 can be prepared, for example, using the methods described in Reilly et al., "Amino Acid Residues 1101-1105 of the Isotypic Region of Human C4B Is Important to the Covalent Binding Activity of Complement Component C4," *Journal of Immunology*, 147(9):3018-3023 (1991) and Kozlov et al., "Inhibition of the binding and activation of the first component of human complement. The effect of synthetic peptides, immunoglobulin fragments and various proteins," *Biokhimiia*, 51(5):707-718 (1986), which are hereby incorporated by reference. Alternatively, the aforementioned antigenic C1q, C2, and C4 proteins can be obtained from commercial sources or other sources. For example, antigenic C1q and C4 proteins can be obtained from Quidel Corporation (San Diego, Calif.).

Alternatively, the aforementioned anti-C1q antibodies, anti-C2 antibodies, and anti-C4 antibodies can be obtained from commercial sources or other sources. For example, monoclonal and polyclonal anti-C1q and C4 can be obtained from Quidel Corporation (San Diego, Calif.).

Still alternatively, the aforementioned anti-C1q antibodies, anti-C2 antibodies, and anti-C4 antibodies can be produced from hybridoma cell lines available from the ATCC. For example, anti-C1q monoclonal antibodies can be produced from hybridoma cell line 4A4B11, which is available from the American Type Culture Collection ("ATCC") (Manassas, Va.) (ATCC No. HB-8327, which is hereby incorporated by reference); or the anti-C1q monoclonal antibodies can be produced from hybridoma cell line 12A5B7, which is available from the ATCC (ATCC No. HB-8328, which is hereby incorporated by reference).

Examples of other compounds that inhibit the subject's classical complement pathway which can be used in the practice of methods of the present invention include synthetic peptide inhibitors of C1q, C2, and/or C4. As discussed above, these synthetic peptide inhibitors can be selective (e.g., to C1q) and/or specific (e.g., to C1q). Synthetic peptide inhibitors of C1q, C2, or C4 can be prepared by selecting peptide sequences from various phage-displayed peptide libraries on the basis of phage binding to C1q, C2, or C4, respectively.

Examples of other compounds that inhibit the subject's classical complement pathway which can be used in the practice of the methods of the present invention include C1q receptor blocking antibodies. The C1q receptor blocking antibodies can be selective for the C1q receptor, or they can be specific for the C1q receptor, or both. The C1q receptor blocking antibodies can be polyclonal or monoclonal, and these polyclonal or monoclonal C1q receptor blocking antibodies can be made, for example, using the any of the methods described hereinabove for making anti-C1q antibodies, except, of course, that, antigenic C1q receptor is used as the immunogen in place of antigenic C1q. Alternatively, suitable C1q receptor blocking antibodies can be obtained from commercial and other sources, for example, as compiled in the Hybridoma Data Bank ("HDB"), e.g., HBD Accession Nos. 152, 153, and 5370. Illustratively, suitable C1q receptor blocking antibodies can be obtained from Chemicon International, Inc. (Temecula, Calif.). The polyclonal or monoclonal C1q receptor blocking antibodies can be humanized, for example, using the methods described hereinabove.

Examples of still other compounds that inhibit the subject's classical complement pathway which can be used in the practice of methods of the present invention include those which inhibit macrophage C1q secretion. Examples of such compounds include 3,4-dehydro-DL-proline ("DHP") and 2,2'-dipyridyl.

The aforementioned antibodies and other compounds can be administered to the subject by any conventional route, and they can be made up in any suitable dosage form appropriate for the desired use. Examples of suitable dosage forms include oral, parenteral, or topical dosage forms.

Illustratively, suitable dosage forms for oral use include tablets, dispersible powders, granules, capsules, suspensions, syrups, and elixirs. Inert diluents, carriers, and other excipients for tablets include, for example, calcium carbonate, sodium carbonate, lactose, and talc. Tablets may also contain other excipients, such as granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents, carriers, and other excipients which may be used in capsules include, for example, calcium carbonate, calcium phosphate, and kaolin. Suspensions, syrups, and elixirs may contain conventional excipients, for example, methyl cellulose, tragacanth, sodium alginate, wetting agents (such as lecithin and polyoxyethylene stearate), and preservatives (such as ethyl-p-hydroxybenzoate).

Dosage forms suitable for parenteral administration include solutions, suspensions, dispersions, emulsions, and the like. They may also be manufactured in the form of solid compositions which can be dissolved or suspended in sterile injectable medium immediately before use. They may contain suspending or dispersing agents or other excipients known in the art. Examples of parenteral administration are intraventricular, intracerebral, intramuscular, intravenous, intraperitoneal, rectal, and subcutaneous administration.

In addition to the above, generally non-active components of the above-described formulations, these formulations can include other active materials, for example, active materials which have been identified as useful in the treatment of autoimmune disorders or conditions or in the alleviation of symptoms associated therewith. These active materials can be broad-based, such as those that are useful in the treatment of a variety of autoimmune disorders or conditions or in the alleviation of symptoms associated with a variety of autoimmune disorders or conditions; or they may be more specific, for example, as in the case where the other active material is specific for the treatment of the particular autoimmune disorder or condition with which the subject is afflicted or for the alleviation of symptoms associated with the particular autoimmune disorder or condition. As further illustration of the active materials that can be additionally included in the above-described formulations (i.e., in addition to the antibodies and other compounds and in addition to non-active components), there can be mentioned active materials that are conventionally employed to suppress other types of graft rejection (i.e., other than hyperacute graft rejection).

It will be appreciated that the actual preferred amount of compound to be administered according to the present invention will vary according to the particular compound, the particular composition formulated, and the mode of administration. Many factors that may modify the action of the compound (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests.

The present invention, in yet another aspect thereof, relates to a composition that includes a specific inhibitor of C1q and a pharmaceutically acceptable excipient. Examples of suitable specific inhibitors of C1q include anti-C1q antibodies, such as anti-C1q monoclonal antibodies and anti-C1q polyclonal antibodies. The anti-C1q antibodies can be prepared by the methods described hereinabove, or they can be obtained commercially or from other sources. The anti-C1q antibodies used in the compositions of the present invention can be a chimeric humanized anti-C1q antibody, prepared, for example, in accordance with the methods discussed hereinabove. The composition of the present invention further includes (i.e., in addition to the specific inhibitor of C1q) a pharmaceutically acceptable excipient. Examples of suitable pharmaceutically acceptable excipients include sterile liquid pharmaceutically acceptable carriers and diluents, non-sterile liquid pharmaceutically acceptable carriers and diluents, sterile solid pharmaceutically acceptable carriers and diluents, and non-sterile solid pharmaceutically acceptable carriers and diluents. Other suitable pharmaceutically acceptable excipients which can be used in the compositions of the present invention include those discussed above with regard to dosage forms.

The present invention is further illustrated with the following examples.

EXAMPLES

Example 1

Overview of the Examples, MG, EAMG, the Complement System, and the Role of Complements in MG and EAMG To delineate the importance of the classical and lytic complement pathways in experimental autoimmune myasthenia gravis ("EAMG") pathogenesis, we first induced EAMG in C3 or C4 gene knockout ("KO") mice with acetylcholine receptor (AChR) immunization and observed that these strains of mice were highly resistant to EAMG induction. Secondly, we performed EAMG prevention experiments on wild-type C57BL/6 (B6) mice using anti-C1q antibodies ("anti-C1q") and observed that this treatment efficiently prevented the induction of EAMG. Examination of immunological parameters revealed that neither C4 KO mice nor anti-C1q treated mice developed prominent immunodeficiency. Thus, our studies have shown that anti-C1q treatment barely interferes with very few of the immunological factors and does not cause prominent immunodeficiency, but still prevent the generation of EAMG.

Myasthenia gravis (MG) is an autoimmune neuromuscular disease. Neuromuscular transmission fails in MG because of decreased sensitivity of the postsynaptic membrane to the neurotransmitter acetylcholine (ACh), which results from a loss of acetylcholine receptors (AChRs) due to a T-cell and B-cell mediated autoimmune attack against the AChR (Christadoss et al., "Immunotherapy for Myasthenia Gravis: a Murine Model," *J. Immunol.*, 136(7):2437-2440 (1986), which is hereby incorporated by reference). An experimental model of MG (EAMG) can be induced in several mammalian species by inoculation of small quantities of electric organ AChR of electric rays (*Torpedo californica*) in adjuvants.

Anti-AChR antibodies are found in about 90% of MG patients, and these antibodies, together with complements (activated by antibody-AChR complex), are implicated as major constituents of the pathogenetic events leading to neuromuscular junction ("NMJ") destruction in both MG and EAMG. Antibodies are suggested to take part in functional AChR loss by blocking AChR, by increasing AChR endocytosis, or by activating the complement-mediated inflammatory destruction of NMJ (Sahashi et al., "Ultrastructural Localization of Immune Complexes (IgG and C3) at the End-Plate in Experimental Autoimmune Myasthenia Gravis," *J. Neuropathol. Exp. Neurol.*, 37(2):212-223 (1978), which is hereby incorporated by reference). However, their serum levels are not correlated with the clinical severity of disease in both MG and EAMG (Nicholson et al., "Acetylcholine Receptor Antibodies in the Diagnosis and Management of Myasthenia Gravis," *Clin. Exp. Neurol.*, 18:61-69 (1981, which is hereby incorporated by reference). This suggests that there may be other critical factors (e.g. complements, cytokines), which contribute to MG and EAMG induction.

The complement system is part of the innate immune system and consists of many proteins that act as a cascade, where each enzyme acts as a catalyst for the next. The complement system is illustrated in FIG. 1. In FIG. 1, grey solid boxes associated with complement factors C4b, C3, and C5 indicate that the importance of these complement factors have been previously studies in our laboratory. As FIG. 1 illustrates, activation of the complement cascade is launched via three separate complement pathways (classical, mannose binding lectin ("MBL"), and alternative pathways). Predominantly, classical pathway is activated by immune complexes, whereas the other two pathways are activated by various pathogens as well as tumor cells, bacterial products, etc. All pathways merge in the lytic pathway, and, irrespective of which pathway is activated, C3 is finally triggered to initiate the activation cascade of lytic pathway that ends with the formation of a membrane attack complex ("MAC").

The proposition that anti-AChR antibodies destroy AChRs located at the NMJ via the complement system is based upon the observation that IgG, C3, and MAC are co-localized at the NMJs of MG patients (Engel et al., "Immune Complexes (IgG and C3) at the Motor End-Plate in Myasthenia Gravis: Ultrastructural and Light Microscopic Localization and Electrophysiologic Correlations," *Mayo Clin. Proc.*, 52(5):267-280 (1977); and Tsujihata et al., "Diagnostic Significance of IgG, C3, and C9 at the Limb Muscle Motor End-Plate in Minimal Myasthenia Gravis," *Neurology*, 39(10):1359-1363 (1989), which are hereby incorporated by reference). So, plausibly, anti-AChR antibodies activate the complement cascade (possibly the classical pathway since this is activated by immune complexes) to induce MAC, which eventually destroys the NMJ. There is substantial evidence that complements play a very important role in the immunopathogenesis of EAMG. C5 deficiency in mice can prevent EAMG development (Christadoss, "C5 Gene Influences the Development of Murine Myasthenia Gravis," *J. Immunol.*, 140(8):2589-2592 (1988), which is hereby incorporated by reference); and inhibition of C3 by cobra venom factor inhibits disease induction. Collectively, these reports show that, at least in the murine model of MG, activation of MAC by the complement system is imperative for muscle AChR loss and, thus, for MG induction.

Example 2

Severity of EAMG in RIIIS/J Mice Is Associated with Increased Production of C1q-Conjugated Immune Complexes and C3

We worked on a mouse strain called RIIIS/J to explore the factors that might be related with increased susceptibility to MG in this strain. We immunized RIIIS/J mice, B10.RIII mice (having the same MHC haplotype H-2r), F1 mice (produced by crossing RIIIS/J and B10.RIII mice), and B6 mice (as a control) with AChR. Among all these strains of mice, RIIIS/J mice had significantly earlier EAMG onset and higher incidence and severity of EAMG (Tuzun et al., "Circulating Immune Complexes Augment Severity of Antibody-Mediated Myasthenia Gravis in Hypogammaglobulinemic RIIIS/J Mice," *J. Immunol.*, 172(9):5743-5752 (2004), which is hereby incorporated by reference).

Although functioning of MHC molecules are imperative for EAMG induction, and, thus, EAMG in RIIIS/J mice should be associated with MHC molecules, we suggested that increased EAMG incidence and severity of RIIIS/J mice is associated with a non-MHC factor(s) as well since B10.RIII mice (having comparable incidence and severity to B6 mice and lower incidence and severity as compared to RIIIS/J mice) share the same MHC haplotype with RIIIS/J mice.

Figure 2A:
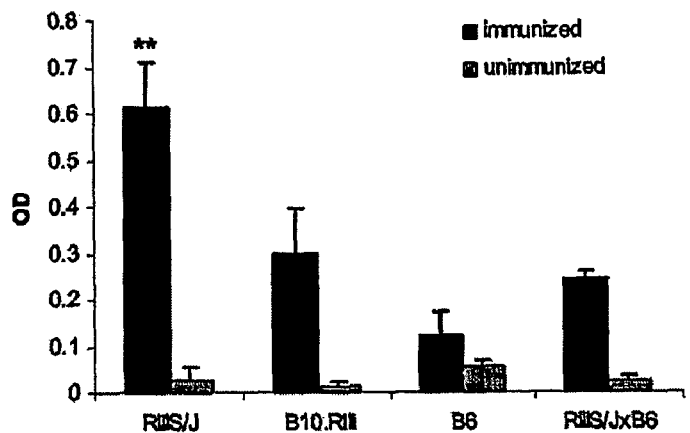
FIGS. 2A-2B are bar graphs showing serum C1q-circulating immune complex ("CIC") levels (FIG. 2A) and serum C3 levels (FIG. 2B) in various mice.
Figure 2B:
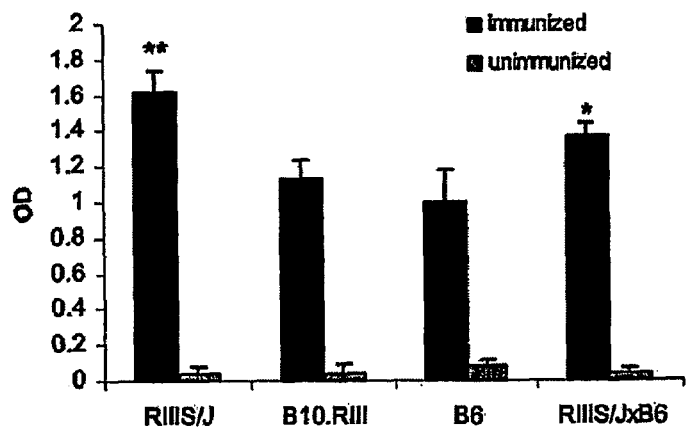
Figure 2C:
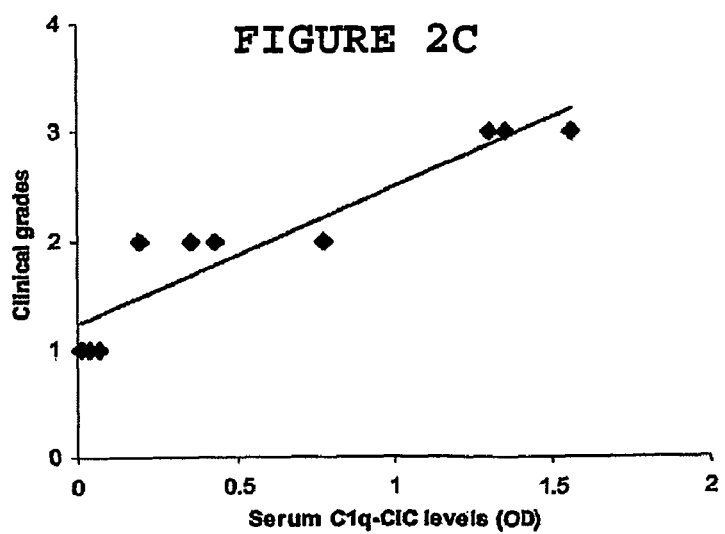
FIG. 2C is a graph showing experimental autoimmune myasthenia gravis ("EAMG") severity as a function of serum CIC levels in RIIIS/J mice.

Among other factors, increased EAMG incidence and severity of RIIIS/J mice were associated with increased CD4+ lymph node cell counts and elevated serum C3 and C1q-conjugated immune complex ("C1q-CIC") levels, as shown in FIGS. 2A and 2B. Moreover, serum C1q-CIC levels were significantly correlated with the clinical severity of EAMG in RIIIS/J mice, as shown in FIG. 2C.

Figure 3:
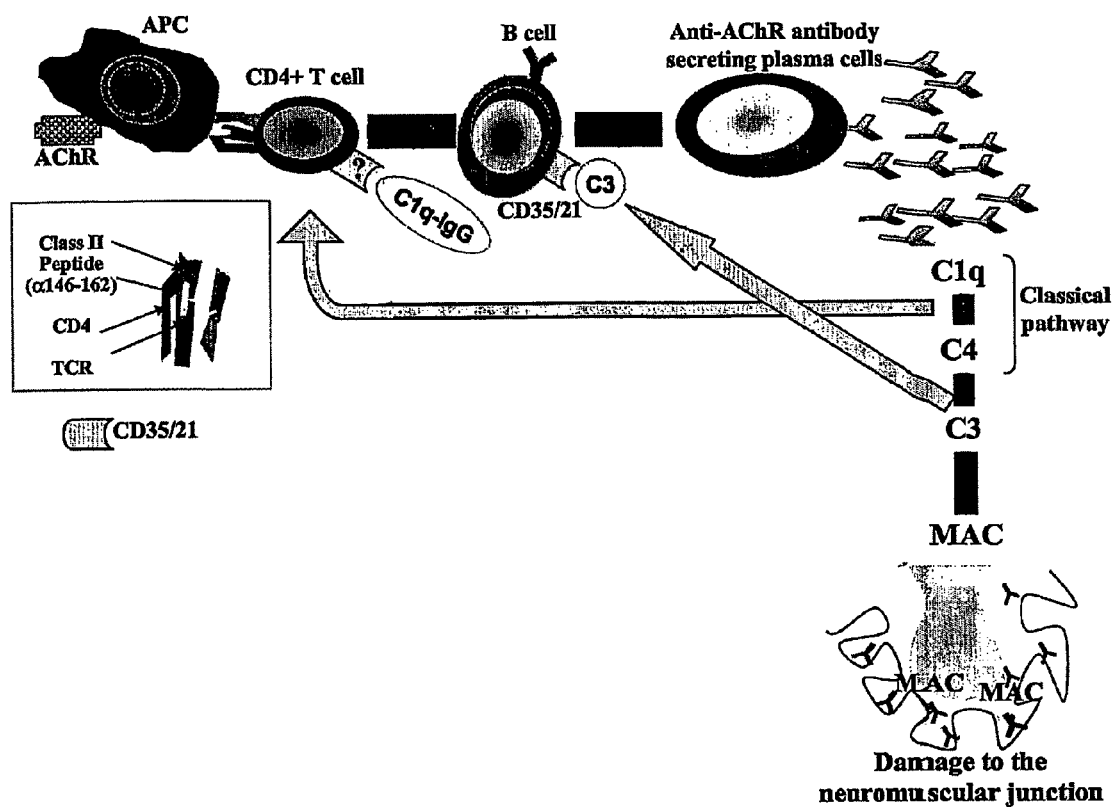
FIG. 3 is a graphic illustrating a hypothetical mechanism of EAMG immunopathogenesis.
Figures 6A, 6B, 6C, 6D:
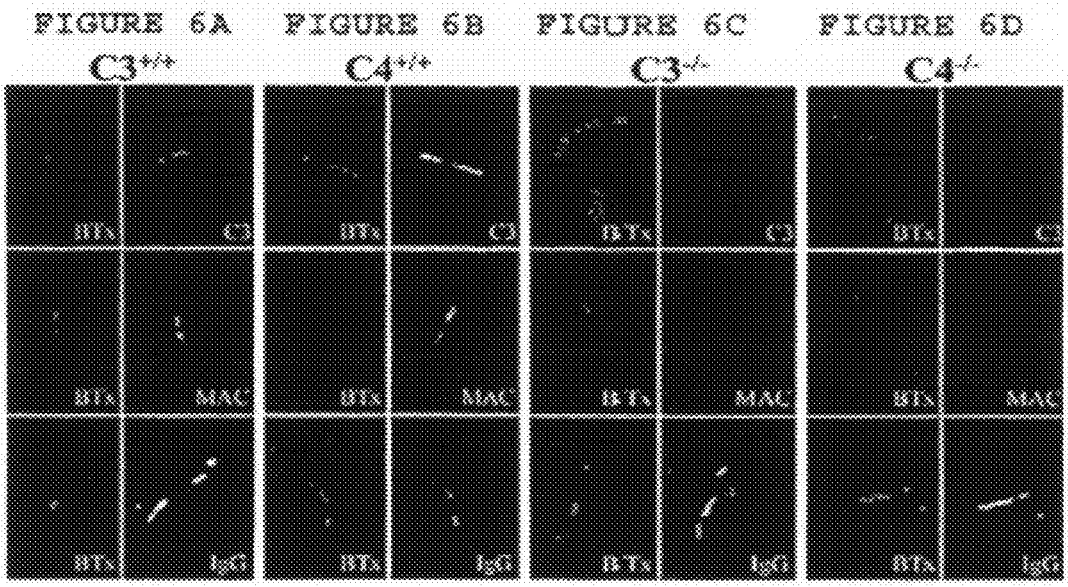
FIGS. 6A-6D are images of frozen muscle sections of $C3^{+/+}$ (FIG. 6A), $C4^{+/+}$ (FIG. 6B), $C3^{-/-}$ (FIG. 6C), and $C4^{-/-}$ (FIG. 6D) mice double-stained with α-bungarotoxin ("α-BTx") (which binds to neuromuscular junction ("NMJ")) and antibodies directed against either IgG, C3, or membrane attack complex ("MAC").

Our findings led us to suggest increased CD4+ T cells as the pivotal factor for increased EAMG incidence. These cells showed their effects possibly by increasing anti-AChR IgG levels and thus inducing a more severe form of EAMG. C3 and C1q-CIC are known to boost the production and proliferation of B and T cells, respectively. Altogether, C3, T cells, and antigen-specific IgG appear to enhance each other's production, creating a vicious circle and thus augmenting clinical disease. Such a hypothetical scenario of EAMG immunopathogenesis is depicted in FIG. 3. Building on this hypothetical scenario, we further hypothesized that one way of breaking this circle would be to decrease C3 levels by blocking the classical pathway.

Example 3

Role of the Classical Complement Pathway in EAMG

To delineate the role of classical complement pathway in EAMG, we immunized C4 gene KO mice with AChR in CFA.

C3 gene KO mice were used as positive control since C3 is a central complement factor and the initiator of the lytic pathway and C5 (another factor of the same pathway) deficient mice are highly resistant to EAMG (Christadoss, "C5 Gene Influences the Development of Murine Myasthenia Gravis," *J. Immunol.*, 140(8):2589-2592 (1988), which is hereby incorporated by reference). To induce EAMG, $C3^{-/-}$, $C3^{+/-}$, $C3^{+/+}$, $C4^{-/-}$, $C4^{+/-}$, and $C4^{+/+}$ mice were immunized with AChR in CFA. $C3^{-/-}$ or $C4^{-/-}$ mice were highly resistant to EAMG (p values for clinical incidences, as compared to control littermates, were 0.0001 and 0.0005), whereas the disease incidences for $C3^{+/-}$, $C3^{+/+}$, $C4^{+/-}$, $C4^{+/+}$ mice were 63%, 86%, 56%, and 88%, respectively (FIGS. 4A-4D). These data provide the first direct genetic evidence for the involvement of C3, C4, and, thus, the classical complement pathway in the development of clinical EAMG following immunization with AChR.

AChR-immunized $C4^{-/-}$ mice possessed similar amounts of total anti-AChR IgG levels in their serum samples as their control $C4^{+/+}$ littermates, whereas $C3^{-/-}$ mice displayed suppressed anti-AChR IgG production (p=0.0049) (FIG. 5A). On the other hand, IgG2b production against AChR was inhibited significantly in both $C3^{--}$ (p=0.047) and $C4^{-/-}$ mice (p=0.029) (FIG. 5C). These results reveal that, in $C4^{-/-}$ mice, EAMG resistance may also be related with diminished levels of complement-binding IgG2b antibodies. Total serum IgG and anti-AChR IgG1 levels were similar to those of control littermates in $C4^{-/-}$ mice (FIGS. 5B and 5D).

To further clarify the importance of C3 or C4 deficiency in EAMG resistance despite the presence of serum anti-AChR IgGs, we double-stained frozen muscle sections of all strains of mice with α-bungarotoxin ("α-BTx") (which binds to NMJ) and antibodies directed against either IgG, C3, or MAC. All mice displayed IgG deposits on the NMJ and all $C3^{+/+}$ and $C4^{+/+}$ littermates had C3 and MAC deposits, whereas C3 and MAC deposits could not be detected on the NMJ of $C3^{-/-}$ and $C4^{-/-}$ mice (FIGS. 6A-6D). The absence of C3 and MAC deposits, despite the presence of IgG on the NMJ of $C3^{-/-}$ and $C4^{-/-}$ mice suggests that C3 and MAC are playing a critical role in NMJ destruction in EAMG. Additionally, IgG bound to the NMJ without complement is not sufficient to induce optimal AChR destruction and clinical EAMG.

Thus, C4 gene deficiency prevented the induction of EAMG, without significantly affecting IgG production and with slight decreases in anti-AChR IgG2b levels.

Further details with regard to the experiments described in this Example 3 can be found in Tuzun et al., "Genetic Evidence for Involvement of Classical Complement Pathway in Induction of Experimental Autoimmune Myasthenia Gravis," *J. Immunol.*, 171(7):3847-3854 (2003), which is hereby incorporated by reference.

Example 4

The Hypothesis and In Vivo Testing Thereof

The experiments described in Example 3 suggest that classical complement pathway may be critical for the development of EAMG and, in mice with complement C4 gene deficiency, the disease incidence and severity can be extremely low. Based on these results, we hypothesized that inhibition of the classical complement pathway would prevent and suppress established EAMG. To analyze the role of acquired classical complement deficiency, we planned to test the hypothesis that in vivo C1q depletion, achieved by administration of anti-C1q, would prevent induction of EAMG by AChR immunization in CFA and also suppress the established disease. The prevention experiments are set forth in Example 5, and the therapeutic treatment experiments are set forth in Example 6.

Example 5

In Vivo Prevention Experiments

We obtained anti-C1q (mouse anti-human IgG) from hybridoma cell line 4A4B11 (ATCC Accession No. 1000617). The antibodies were acquired from the medium of the cultured cells, and they were purified by an affinity column procedure.

Our preliminary studies showed that administration of this antibody (0.2 mg/injection, twice weekly, starting 10 days before first immunization) caused a measurable decline in the clinical incidence and severity of EAMG. A non-specific mouse IgG antibody (Sigma) (applied in the same dosages as anti-C1q) was used as a negative control in all experiments.

Eight of each anti-C1q-treated and control-antibody-treated B6 mice (Jackson Laboratory) were immunized s.c. in foot pads and shoulders with 20 μg Torpedo AChR in CFA on day 0 and then were reimmunized s.c. in shoulders and thighs with the same amount of antigen on day 30. Anti-C1q or control antibody treatment (i.p.) was started 10 days before the first immunization with AChR in CFA with an initial dose of 200 μg. Then, treatment was continued with 100 μg/injection, twice weekly. Mice were screened for the development of clinical EAMG and were bled for serum on days 0, 15, and 45.

Figure 7A:
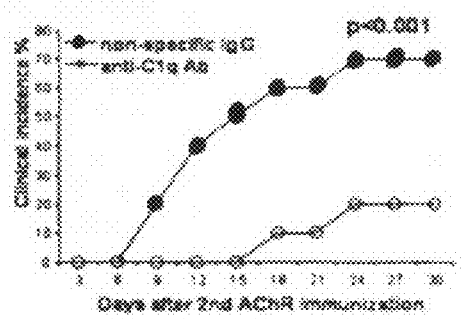
FIGS. 7A-7C are graphs showing that, relative to control IgG-treated mice, anti-C1q mice exhibit reduced incidence of EAMG induction (FIG. 7A), that anti-C1q-treated mice have less severe EAMG (FIG. 7B), and that anti-C1q-treated mice have significantly higher average grip strengths (FIG. 7C).
Figure 7B:
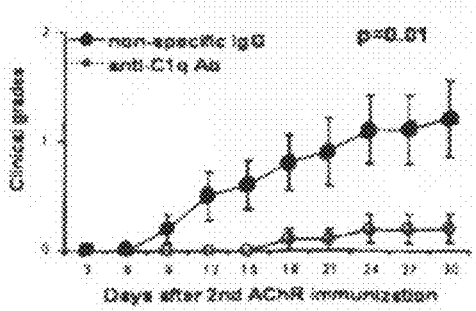
Figure 7C:
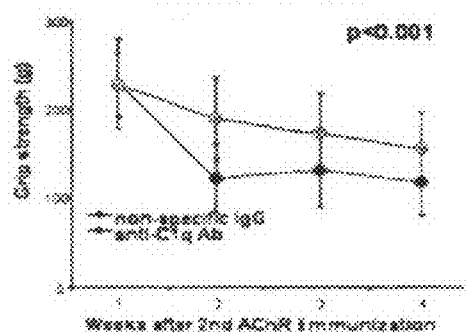

Anti-C1q treatment protected mice against EAMG induction, as shown in FIG. 7A. Briefly, EAMG incidence was 20% in anti-C1q-treated mice vs. 70% in control IgG-treated mice (p<0.0001). Also, as shown in FIG. 7B, anti-C1q-treated mice had less severe EAMG (i.e., significantly lower average clinical grades, p=0.01), compared to their control IgG-treated mice counterparts. Moreover, the average grip strength (an objective measure of muscle strength measured in a grip strength meter) of anti-C1q-treated mice remained significantly higher than that of control IgG-treated mice (p<0.001) (FIG. 7C). However, anti-C1q-treated mice still had lower average grip strength as compared to before-treatment values, suggesting, perhaps, that anti-C1q-treatment is considerably preventing EAMG induction, but, at the same time, the clinical worsening and possibly the NMJ AChR loss is going on, probably at a slower pace, as compared to control mice.

FIGS. 8A-8D show cytokine production profiles of anti-C1q-treated mice and control IgG-treated-mice. Suppression of EAMG in anti-C1q-treated mice was associated with lower IL-6 and IFN-γ production by AChR- and/or immunodominant peptide α146-162-stimulated cultured lymph node cells (p<0.05, FIGS. 8B and 8D). Interestingly, AChR-immunized C3 KO mice also had lower IL-6 and IFN-γ levels in their cultured lymph node cell supernatants. This is a notable finding, since IL-6 and IFN-γ are important factors in EAMG pathogenesis (Karachunski et al., "Absence of IFN-gamma or IL-12 Has Different Effects on Experimental Myasthenia Gravis in C57BL/6 Mice," *J. Immunol.*, 164(10):5236-5244 (2000); and Deng et al., "Resistance to Experimental Autoimmune Myasthenia Gravis in IL-6-Deficient Mice Is Associated with Reduced Germinal Center Formation and C3 Production," *J. Immunol.*, 169(2):1077-1083 (2002), which are hereby incorporated by reference).

Additionally, anti-C1q-treated mice had lower C3, IgG, and MAC deposits at their NMJs (FIG. 9).

Figure 10A:
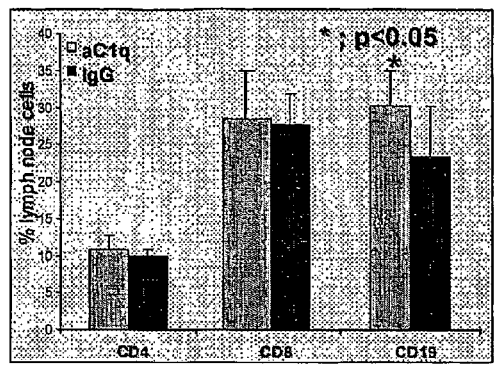
FIGS. 10A-10C are bar graphs and images showing the results of flow cytometry analysis of the lymph node cells and immunohistochemistry performed on paraffin-embedded spleen sections of anti-C1q-treated mice and control IgG-treated mice.
Figure 10B:
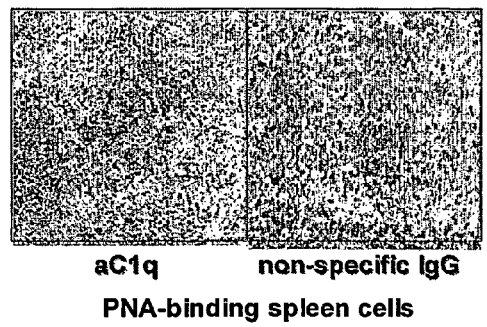
Figure 10C:
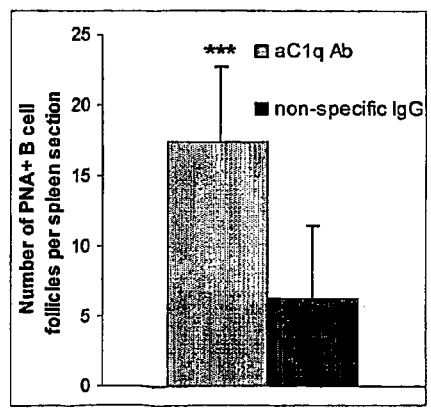

Flow cytometry analysis of the lymph node cells and immunohistochemistry performed on paraffin-embedded spleen sections revealed normal T cell and elevated B cell counts in lymph node cells (FIG. 10A) and normal PNA+ germinal center follicles in spleen sections of anti-C1q-treated mice (FIGS. 10B and 10C).

Figure 11:
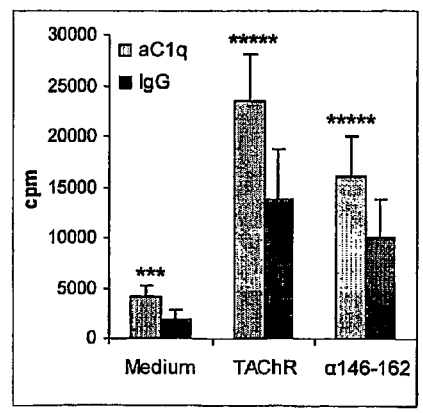
FIG. 11 is a bar graph showing lymph node cell proliferation in anti-C1q-treated mice and control IgG-treated mice.

AChR-stimulated lymphocyte proliferation was not affected by anti-C1q-treatment (FIG. 11), suggesting that T and B cell functions were preserved. Interestingly, both PNA+ spleen germinal center follicles and proliferation capacity of lymph node cells were increased in anti-C1q-treated cells, which might be a reflection of stimulatory effects of increased levels of immune complexes on T and B cell proliferation.

On the other hand, anti-C1q-treated mice had an overall enhancement in the humoral response characterized by increased serum anti-AChR antibody levels (IgM, IgG, IgG1 isotypes) (FIGS. 12A-12F) and increased serum C1q, C3, and C3-conjugated immune complex levels (FIGS. 13A-13D). All experiments were repeated at least twice to ensure reproducibility of the data.

Despite elevated antibody and complement response, anti-C1q treatment ameliorated EAMG. This suggests that anti-C1q treatment might not be preventing EAMG by classical complement pathway blockade. Anti-C1q might be increasing the half-lives of C1q molecules or triggering a compensatory increase in C1q production and thus increasing classical pathway activation and consequent C3 production. Increased C3 and immune complex levels might be enhancing B cell antibody production. anti-C1q might rather be preventing EAMG induction by competing with immune complexes in the circulation and partially reducing lymph node cell IL-6 and IFN-γ production. With a similar mechanism, anti-C1q might be preventing immune complex deposition and complement activation, which would eventually cause NMJ destruction (a hallmark of MG pathology). Then again, it is noteworthy that anti-C1q treatment does not cause a reduction in lymph node B and T cell counts, in sharp contrast with the currently available immunosuppressive drugs (e.g. steroids, azathioprine), which decrease T and B cell counts significantly.

Example 6

In Vivo Treatment Experiments on Ongoing Clinical EAMG

A preliminary treatment experiment was carried out by administering anti-C1q after two immunizations to test whether C1q inhibition is capable of treating EAMG after generation of autoimmune response to AChR, simulating MG patients after diagnosis. For this purpose, a group of B6 mice were immunized with 20 μg AChR in CFA on days 0 and 30. Five of these mice with lowest grip strength and/or Grade 2 or 3 disease were selected for treatment experiments. One group (n=3) of mice with Grade 2 or 3 disease was treated i.p. with anti-C1q and a second group (n=2) was treated with the control antibody (non-specific mouse IgG). The treatment schedule was same as that performed in prevention studies (initial dose of 200 μg, then, 100 μg/injection, twice weekly). Before anti-C1q treatment and on days 15 and 45 after anti-C1q treatment, mice were bled via tail vein. Mice were regularly screened for clinical scores, and, 35 days after the initiation of anti-C1q treatment, they were terminated and immunopathological examinations were performed.

Although this is an experiment conducted with small numbers of mice for both groups, some of the preliminary results were noteworthy.

Figure 14:
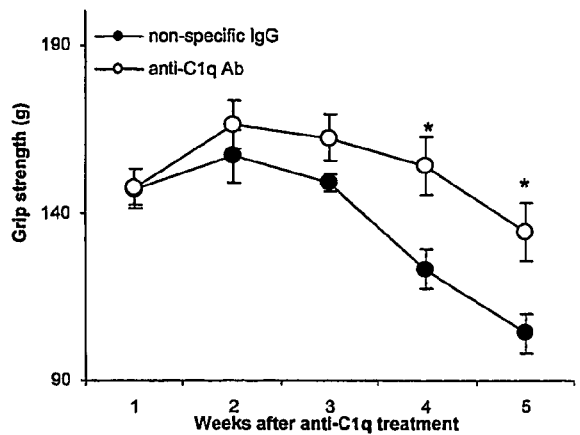
FIG. 14 is a graph showing average grip strengths of mice afflicted with ongoing EAMG while being treated with anti-C1q or control IgG at various times during the treatment period.

The anti-C1q-treatment decreased the severity of EAMG in one out of three mice from Grade 2 to Grade 1, whereas the clinical condition of one mouse remained stable and 1 mouse continued to clinically deteriorate. Both mice in the control group went on developing more severe disease (one mouse developed Grade 2 disease and the other Grade 3). However, the average of the grip strengths in anti-C1q-treated mice was significantly higher than the control mice (FIG. 14).

Figure 15:
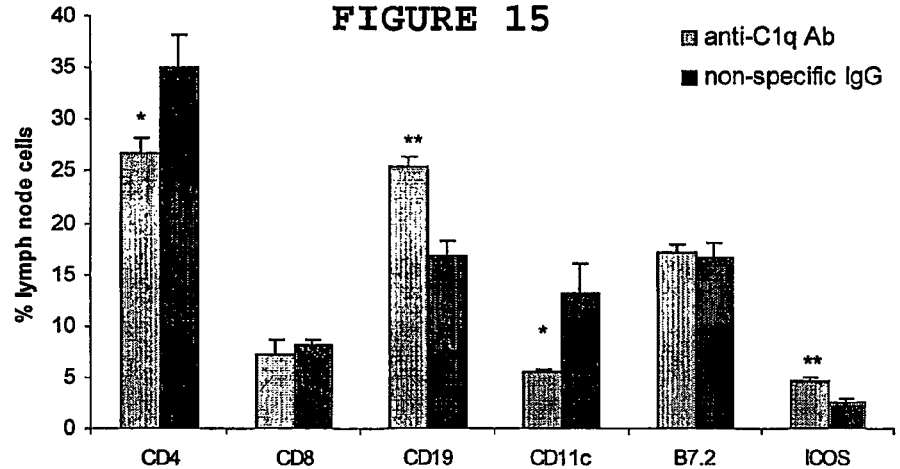
FIG. 15 is a bar graph showing lymph node cell profiles of mice afflicted with ongoing EAMG after treatment with anti-C1q or control IgG.
Figure 16:
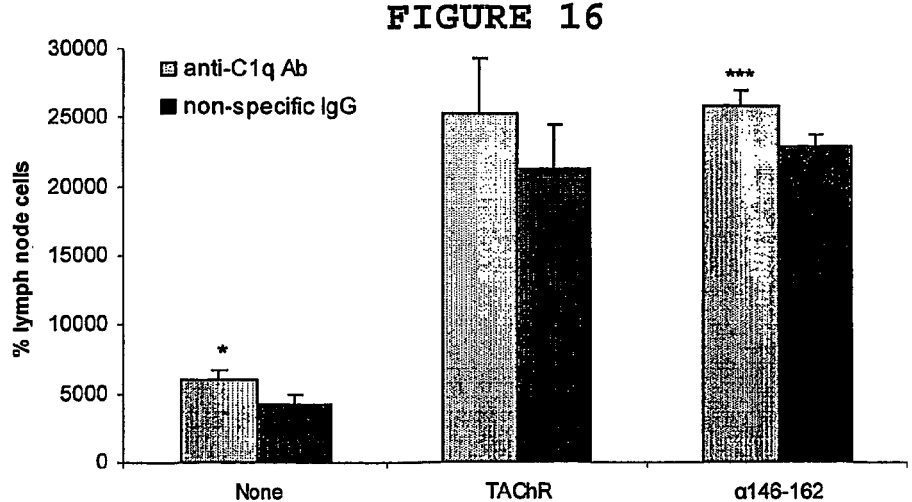
FIG. 16 is a bar graph showing lymph node cell proliferation in mice afflicted with ongoing EAMG after treatment with anti-C1q or control IgG.

A lymph node cell profile of the anti-C1q-treated (n=3) and control antibody-treated (n=2) mice is presented in FIG. 15. As FIG. 15 shows, anti-C1q-treatment was associated with the suppression of CD11c+ lymph node dendritic cells and an increase in CD19+ and ICOS+ cells in the lymph node. Dendritic cell suppression was particularly noteworthy since C1q is known to have inhibitory effects on dendritic cell functions. This might be associated with increased serum C1q levels due to anti-C1q treatment. Increase in CD19+ cells was similar to the increase observed in the prevention studies, proving, once again, the B cell stimulating potential of anti-C1q. In line with this finding, and similar to prevention studies, lymphocyte proliferation was significantly more pronounced in anti-C1q treated mice as compared to control mice (FIG. 16).

Example 7

Discussion of the In Vivo Results

As observed from the in vivo prevention and treatment experiments described in Examples 5 and 6, anti-C1q appears to constitute a useful method to decrease the severity and incidence of EAMG without abolishing humoral immunity and antibody production and only partially blocking T cell cytokine production.

As noted above, anti-C1q treatment appears to increase serum C1q levels rather than decreasing them. Since C1q plays important roles in self-tolerance, clearance of immune complexes and apoptotic cells, and defense against infections, having increased serum C1q and C3 levels might be beneficial for the MG patients.

EAMG preventing efficiency obtained in the first two experiments proved to be more prominent, and anti-C1q-treated mice had much less severe EAMG. Therefore, anti-C1q therapy may find particular utility during MG remissions to prevent the exacerbation of disease. Currently, in general practice, MG patients who have undergone remission are still treated with very low doses of steroids for the fear of an imminent exacerbation. Anti-C1q may replace this treatment. It can also be used as an adjunct immunotherapy method for MG with acute and/or severe muscle weakness, for example, in addition to steroids and azathioprine. Additionally, increased immune complex levels observed in anti-C1q-treated mice are perturbing and might cause SLE-like immune complex diseases in the long run. In view of this, it may not be wise to attempt anti-C1q treatment in patients with lupus.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. A method for treating myasthenia gravis in a subject, said method comprising:

administering to the subject an anti-C1q antibody which inhibits the subject's classical complement pathway, wherein said anti-C1q antibody is a monoclonal antibody or chimeric humanized antibody thereof that binds C1q.